United States Patent [19]

Tasch et al.

[11] 3,995,739
[45] Dec. 7, 1976

[54] PEELABLE, AUTOCLAVABLE PACKAGING

[75] Inventors: Robert J. Tasch, Lisle, Ill.; Nitidhan P. Patolia, Stamford, Conn.

[73] Assignee: Acme Backing Corporation, Stamford, Conn.

[22] Filed: Dec. 27, 1974

[21] Appl. No.: 536,801

Related U.S. Application Data

[63] Continuation-in-part of Ser. No. 302,926, Nov. 1, 1972, abandoned.

[52] U.S. Cl. .............................. 206/484; 229/48 T; 428/355
[51] Int. Cl.² .................. B65D 65/42; B65D 75/30
[58] Field of Search .......... 206/484, 494, 440, 438, 206/498; 117/122; 229/48 T; 428/355, 514, 510

[56] References Cited

UNITED STATES PATENTS

| | | | |
|---|---|---|---|
| 2,954,116 | 9/1960 | Maso et al. | 206/440 |
| 3,189,174 | 6/1965 | Cormack | 206/498 |
| 3,217,871 | 11/1965 | Lee | 206/440 |
| 3,315,802 | 4/1967 | Lonholdt et al. | 206/63.3 |
| 3,604,616 | 9/1971 | Grief | 206/484 |

*Primary Examiner*—William T. Dixson, Jr.

[57] ABSTRACT

A web of selected sheet materials for conversion into packages for carrying sterile objects such as medical and/or surgical devices, accessories and the like; such packages being initially subjected to dry and steam autoclaving to sterilize the contents thereof and thereafter peelable to allow for access to the contents thereof. The web is coated with a heat sealable composition of a character which has its normal peel characteristic unchanged despite the initial autoclaving operation at elevated temperatures.

6 Claims, 3 Drawing Figures

PEELABLE, AUTOCLAVABLE PACKAGING

This application is a continuation in part of application Ser. No. 302,926, filed November 1, 1972, now abandoned.

BACKGROUND OF THE INVENTION

Packages for carrying sterile articles such as dressings, surgical devices, or the like, are frequently rendered sterile by subjecting the package and its contents to autoclaving temperatures of the order of at least 250° F. It is desirable that such packages be peelable to deliver the contents thereof in a sterile field. Since such packages are normally formed from a web or webs with a coating of peelable heat sealing composition between panel portions of such webs; it has been found that a subsequent autoclaving operation tends to impair or nullify the peel characteristic of the heat sealing composition.

It has been proposed to overcome the undesirable increase in bonding of peelable packaging due to the autoclaving temperatures, by either (1) reducing the initial sealing temperatures, or (2) decreasing pressure of the sealing operation, or (3) shortening the dwell time at the point of seal.

However such expedients, in effect, produce undersealed packages which tend to exhibit leakage in the original seal and impair the maintenance of sterility in the final autoclaved package.

If the usual sealing temperatures, pressures and dwell periods are used; the subsequent autoclaving temperatures can increase the bond of the heat seals, which impairs the peelable characteristic of the autoclaved package.

Accordingly, an object of this invention is to provide a package of the type which must be subject to autoclaving to render the contents thereof sterile; where the peripheral portions of the panels forming the package are secured together by a heat sealing composition which on the one hand forms a uniform tight, non-leaking seal; and on the other hand, such seal is still subject to easy peeling when opening the autoclaved package to gain access to the sterile contents thereof.

Another object of this invention is to provide a package of the character set forth, wherein the sealing composition is constituted primarily of a thermoplastic resin having good seal and peel properties, and a modifier of a plastic character the sealing composition retaining its normal seal and peel properties despite exposure of the sealed packaging to elevated autoclaving temperatures.

Still another object of this invention is to provide packaging of the character described, wherein the heat sealing composition is made up of selected vinyl polymers and a modifier of nitrocellulose; such composition being stable in respect of its sealing and peeling properties despite being subjected to elevated autoclaving temperatures.

Other objects of this invention will in part be obvious and in part hereinafter pointed out.

DESCRIPTION OF THE PREFERRED EMBODIMENTS

The packaging of the instant invention comprises essentially, a substrate in the form of metal foil, supported metal foil or suitable plastic films alone or in combination form to suit the need of the items being packaged and the conditions of use.

The substrate is provided on one side thereof with a coating of a heat sealing composition having a thermoplastic resin base and a modifier which is noncompatible with the resin base. Such coating provides the means for sealing peripheral portions of substrate panels superposed and forming the package.

The nature of the heat sealing composition is such that it may be utilized under normal sealing conditions including sealing temperatures, sealing pressures, and sealing dwells, which are productive of a seal in the finished package which is proof against leakage which render the interior of the package non-sterile, yet allows for easy peeling of the panels to open the package and to gain access to the contents thereof.

Further, such sealing composition allows for autoclaving of the sealed packages at temperatures of at least 250° F. to thereby sterilize the contents thereof, yet leaving the package heat seals substantially unaffected to thereby permit easy peeling of the autoclaved package.

Figure 1:
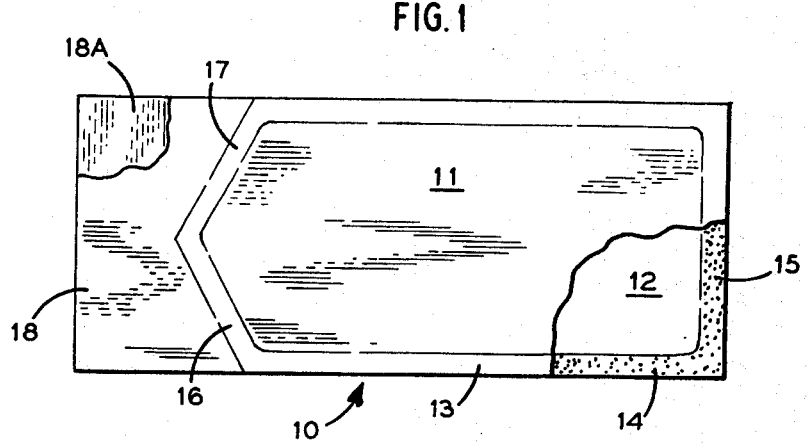
FIG. 1 is a top plan view of a package embodying the invention; with parts broken away.
Figure 2:
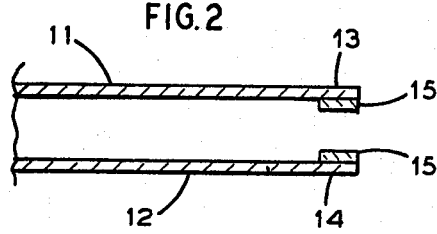
FIG. 2 is a sectional view showing superposed panel portions of the package.

Thus, as shown in FIG. 1, 10 designates a package made in accordance with the instant invention. Package 10 is formed from a flexible web or webs such as metal foil or the like; with opposed panels of such webs indicated at 11, 12. The panels 11, 12 are precoated on the inner surface or surfaces or, only along peripheral portions 13, 14 thereof with a thermoplastic seal coating 15. The peripheral portions 13, 14 may include chevron portions indicated at 16, 17, at one end of the package; leaving unsecured tab portions 18, 18A to provide means for peeling panels 11, 12 apart when the contents of the package 10, not shown are to be exposed for removal from the package.

The thermoplastic seal coating 15 is formed by mixing polyvinyl chloride with a plastic non-compatible therewith, more particularly nitrocellulose. Thus, the polyvinyl chloride dissolved in methyl ethyl ketone is mixed with a solution of 30 second nitrocellulose in a mixture of toluol and methyl ethyl ketone or other suitable solvent.

The PVC solution contains 25% solids by weight while the nitrocellulose solution contains 17% solids by weight. From 70% to 80% of the PVC solution is mixed with from 30% to 20% of the nitrocellulose solution. Preferably 75% of the PVC solution is mixed with 25% of the nitrocellulose solution.

Since the solvents evaporate after the solution of mixed PVC and nitrocellulose is applied to the substrates 11, 12; the coating 15 is constituted of from 17.5 to 20.0 parts of PVC solids and from 5.1 to 3.4 parts of nitrocellulose solids, all by weight. Preferably, the proportion is 18.75 parts of PVC and 4.25 parts of nitrocellulose, all by weight.

The panels 11, 12 are sealed together after disposing the desired object, not shown, therebetween, by applying heat and pressure to the peripheral portions of the package, in a conventional manner, using the usual pressure sealing dies. The thus sealed packages are autoclaved in dry heat or by steam in the usual manner and, generally at temperatures of from 250° to 275° F.

Despite the relatively high temperatures of the autoclaving operation, the package 10 may be readily opened by peeling panels 11, 12 apart by way of tabs 18, 18A. Thus, the elevated autoclaving temperatures do not increase the adhesion characteristics of the coating 15 beyond the normal, leakage proof property of said coating.

Figure 3:
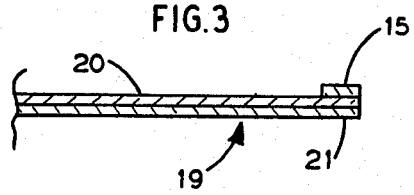
FIG. 3 is a partial sectional view showing an alternative form of web for forming the package.

It is understood that other substrates may be used in forming packages 10. Thus, as shown in FIG. 3, a web 19 may be used to provide a substrate for package 10. The same comprises a very thin metal foil 20, supported on a paper 21 and adhesively secured thereto by suitable adhesives known in the art.

Other substrates may be used including polyester and or selected polyolefin films, polypropylene or high density polyethylene films, in unsupported or laminated form. The coating 15 may also include suitable plasticizers such as dioctyl phthalate and the like.

The coating 15 may be applied over the entire surface of the substrate from which panels 11, 12 are derived, rather then being limited to the peripheral areas, as described above.

The seal coating 15 may also be derived from a composition constituted of a major proportion of polyvinyl acetate and a minor proportion of nitrocellulose. Such composition may be used in forming package 10 and will show good peel properties desite exposure of the package to elevated autoclaving temperatures.

Thus, seal formulations were prepared, as follows:

| | | | |
|---|---|---|---|
| (1) | 70.6% polyvinyl acetate | or | 17.5 parts |
| | 29.4% nitrocellulose (30 second) | | 7.28 parts |
| (2) | 80.0% polyvinyl acetate | or | 20.0 parts |
| | 20.0% nitrocellulose | | 5.0 parts |
| (3) | 76.2% polyvinyl acetate | or | 18.75 parts |
| | 23.8% nitrocellulose | | 5.86 parts |

The foregoing are all in percentages and parts by weight; formulation (3) being preferred.

Packages prepared as previously described; the seal coating 15 having a composition made up of polyvinyl acetate and nitrocellulose, in accordance with formulations (1); (2); and (3); were subjected to elevated autoclaving temperatures to render the contents of the packages sterile.

The autoclaved packages were tested for peelability and found to be within acceptable peel values.

We claim:

1. A heat sealed peelable package sterilized by autoclaving at elevated temperatures comprising a pair of substrates, at least one of said substrates having at least a continuous generally peripheral coating securing said substrates together, said coating comprising about 18.75 parts polyvinyl acetate and about 5.86 parts nitrocellulose, all by weight, said coating retaining its normal peelable adhesive characteristics despite exposure thereof to said autoclaving temperature.

2. A package as in claim 1 wherein at least one of said pair of substrates comprises metal foil.

3. A package as in claim 1 wherein at least one of said pair of substrates comprises metal foil and a supporting layer adhesively secured to said foil.

4. A heat sealed peelable package sterilized by autoclaving at elevated temperatures comprising a pair of substrates, at least one of said substrates having at least a continuous generally peripheral coating securing said substrates together, said coating comprising about 18.75 parts polyvinyl chloride and about 4.25 parts nitrocellulose, all by weight, said coating retaining its normal peelable adhesive characteristic despite exposure thereof to said autoclaving temperature.

5. A package as in claim 4 wherein at least one of said pair of substrates comprises metal foil.

6. A package as in claim 4 wherein at least one of said pair of substrates comprises metal foil and a supporting layer adhesively secured to said foil.

* * * * *